United States Patent [19]

Gray et al.

[11] 4,127,506

[45] Nov. 28, 1978

[54] PHOTOCHEMICAL PREPARATION OF OLEFIN ADDITION CATALYSTS

[75] Inventors: Harry B. Gray, Pasadena; Alan Rembaum, Altadena; Amitava Gupta, Los Angeles, all of Calif.

[73] Assignee: California Institute of Technology, Pasadena, Calif.

[21] Appl. No.: 764,402

[22] Filed: Jan. 31, 1977

Related U.S. Application Data

[63] Continuation-in-part of Ser. No. 666,184, Mar. 12, 1976, abandoned.

[51] Int. Cl.² .................. B01J 31/20; B01J 31/24
[52] U.S. Cl. .................. 252/431 N; 204/159.14; 260/604 HF; 260/605 R
[58] Field of Search ............... 252/429 R, 431 N, 428, 252/432; 204/159.14

[56] References Cited

U.S. PATENT DOCUMENTS

| | | | |
|---|---|---|---|
| 2,480,672 | 8/1949 | Plank | 252/432 X |
| 3,636,159 | 1/1972 | Solomon | 252/431 N X |
| 3,652,676 | 3/1972 | Kahle et al. | 252/431 N X |
| 3,872,026 | 3/1975 | Dunn | 252/431 N X |
| 3,923,533 | 12/1975 | Hammel et al. | 252/432 X |

OTHER PUBLICATIONS

J. Org. Chem., 28 (July, 1963), pp. 1947–1948, Lapporte et al.

*Primary Examiner*—Patrick Garvin
*Attorney, Agent, or Firm*—Marvin E. Jacobs

[57] ABSTRACT

Novel polymer supported catalysts are prepared by photo-irradiation of low valent transition metal compounds such as $Co_2(CO)_8$, $Rh_4(CO)_{12}$ or $Ru_3(CO)_{12}$ in the presence of solid polymers containing amine ligands such as polyvinyl pyridine. Hydroformylation of olefins to aldehydes at ambient conditions has been demonstrated.

19 Claims, 10 Drawing Figures

PHOTOCHEMICAL PREPARATION OF OLEFIN ADDITION CATALYSTS

ORIGIN OF THE INVENTION

The invention described herein was made in the performance of work under a NASA contract and is subject to the provisions of Section 305 of the National Aeronautics and Space Act of 1958, Public Law 83-568 (72 Stat. 435; 42 USC 2457).

CROSS-REFERENCE TO RELATED APPLICATION

This application is a continuation-in-part of Ser. No. 666,184, filed Mar. 12, 1976, now abandoned.

BACKGROUND OF THE INVENTION

1. Field of the Invention

The present invention relates to polymer supported transition metal catalysts and more particularly to the preparation of these catalysts by photoirradiation of the polymer support in the presence of a transition metal compound and to the use of the catalysts in chemical reactions under mild conditions.

2. Description of the Prior Art

The abundant reserves of coal, coupled with the rapid depletion of known oil reserves, mandates that new technology be developed for synthesis of synthetic fuels from coal gases. Hydroformylation, or the oxo reaction of an unsaturated olefinic compound with hydrogen and carbon monoxide to yield an aldehyde, has been known since 1938. This reaction is interesting since a second stage process using hydrogen can convert the aldehyde into the so-called oxo alcohols.

The catalytic mechanism of the oxo process is homogenous in nature and the process was therefore developed using homogenous catalysts such as dicobalt octacarbonyl, $Co_2(CO)_8$ or analogues thereof utilizing other low valent transition metals or replacing one or more of the carbonyl ligands with other ligands such as triphenylphosphine. The process is usually practiced at high temperatures and pressures. Examples of current industrial processes for forming products from coal based raw materials follows:

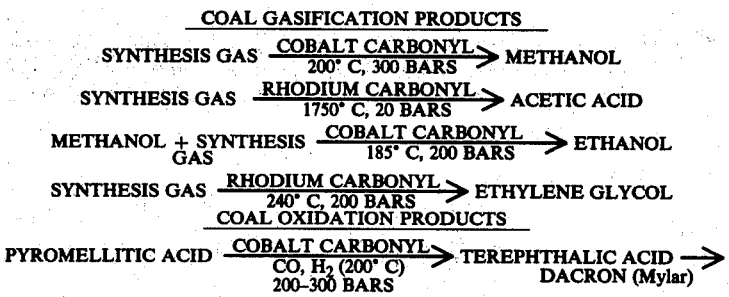

The relative merits of homogeneous and heterogeneous catalysts are well known. Homogeneous catalysts have better defined active sites, usually have all of the metal available for catalysis, and offer steric and electronic environments of the metal atom that can, at least in principle, be varied at will. The major disadvantage of homogeneous catalysts is the need to separate them from reaction products without loss of their valuable metal content. This step can be both complex and expensive. Other disadvantages are that these catalysts are relatively easily deactivated through aggregation or by poisonous by-products or at extreme temperatures. Also corrosion of reactors by metal complexes is common.

The advantages might be retained and the disadvantages removed if the homogeneous catalyst is either impregnated onto a solid support, or in some way chemically bonded to it.

Most workers have used complexes in which phosphine groups are used to link the metal to the solid support. Two types of polymer support, modified polystyrene and silica, have been studied. With polystyrene the form of the polymer can be changed by changing the amount of cross-linking, a feature that appears to have important consequences on the type of catalyst produced. This is the type of support that has been most widely used. Complexes of cobalt carbonyls with polyvinylpyridine have been utilized to thermally catalyze hydroformylation at high temperature and pressure. It has been found that addition of polymer made the system resistant to poisons. However, the catalyst has been shown to be a solution of cobalt hydrocarbonyl and is dissociated from the polymer support. Thus, a disadvantage of thermal hydroformylation using metal polymer species is the gradual loss of metal from the polymer, rendering it commercially unfeasible to utilize expensive metals such as rhodium as a catalyst component.

Hydroformylation under photochemical conditions in solution has also been observed. The overall stoichiometry utilizing $Co_2(CO)_8$ appears to be as follows:

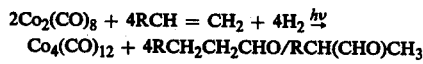

As in thermal catalytic systems, the reaction is inhibited by carbon monoxide. The cobalt dimer is converted in part to the tetramer and is consumed by the process which is therefore not catalytic in the homogeneous phase. The carbonyl group being added to the olefin therefore originates from the cobalt dimer. The tetramer absorbs in the visible at longer wavelengths than the dimer as well as in the same region with higher intensity. Consequently the photoreaction is self-terminating due to the internal filter effect.

Transition metal-phosphinated polystyrene complexes have also been prepared in the presence of light. However, these catalysts though useful in hydrogenation reactions, have not demonstrated hydroformylation activity.

SUMMARY OF THE INVENTION

A new class of catalysts with profound implications for the synthesis of chemical intermediates and fuels from coal based raw materials has been developed in accordance with this invention. The catalyst is synthesized by a photochemical reaction between a low valent transition metal compound and a polymer having amine ligands within or pendant to the polymer backbone. Photochemically generated transition metal species are immobilized on polymer surface and are prevented from losing their activity through dimerization or reaction with impurities. These polymer bound transition metal species then act as catalysts for a wide variety of industrially important reactions e.g., hydrogenation, isomerization, hydroformylation, carbonylation, etc. These anchored catalysts show improved activity and stability compared to the corresponding homogeneous phase catalysts or to prior photoirradiated heterogenous metal-polymer catalysts. Photochemical generation of the catalysts also eliminates the use of high temperatures which is normally needed to generate the catalyst thermally.

Other advantages of the new catalyst are: (a) it can operate at room temperature and atmospheric pressure and thus compares favorably with the best catalyst currently in use, (b) it remains active for a long period of time, (c) it is easily separable from products. Other aspects of the invention relate to synthesis of specially designed, porous and high area polymer supports.

The relatively low pressures in the reaction enable synthesis gas to be introduced directly into the oxo plant and obviates the necessity to use high pressure equipment. This in turn reduces both capital cost and operating costs, as might be expected from the relative simplicity of the techniques employed. The catalyst is much easier to handle during operation.

These and many other objects and many attendant advantages of the invention will become apparent as the invention becomes better understood by reference to the following detailed description when considered in conjunction with the accompanying drawings.

DESCRIPTION OF THE PREFERRED EMBODIMENTS

Figure 1:
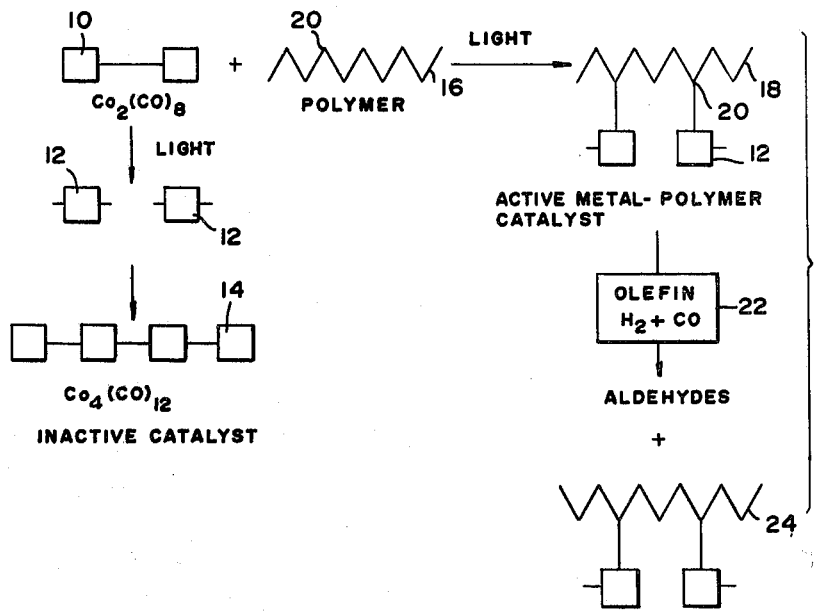
FIG. 1 is a schematic view of the proposed mechanisms for the photo-oxo process and for the phototriggered catalyst process of this invention.

The low valent transition metal compounds are compounds of metals of Groups IV, VI, VII, or VIII of the Periodic Table having a valence lower than the maximum valence coordinated to ligand groups such as carbonyl or trisubstituted phosphines such as triphenyl phosphine. Typical metals are cobalt, nickel, iron, platinum, rhodium, palladium, manganese, chromium, titanium, ruthenium, tantalum, and iridium.

The polymer is a solid support containing amine ligands capable of coordinating with the low valent transition metal preferably tertiary amine such as $-CH_2NMe_2$, $-PhNMe_2$, $-pyridyl$, and the like. The ligand is preferably pendant from the polymer backbone. Representative polymers are cross-linked polystyrenedivinylbenzene copolymers substituted with $-CH_2NMe_2$. Preferred polymers are polyvinylpyridine, polyethylene imine or polyvinylbenzimidazole. Ph is phenyl and Me is methyl.

The polymer must be insoluble in the irradiation reaction media and in the olefin addition reaction media. The polymer support may be in the form of particles, sheets, films, stands, hollow fibers or as a coating on a surface. The polymeric substrate is preferably a high area substrate such as porous particles having a diameter below 1000 microns or coated onto a carrier such as glass particles.

Vinyl pyridine polymers containing at least 30% by weight of vinyl pyridine monomer are preferred due to the ready availability of the pendant pyridyl group for coordination with the transition metal atom. 2-vinyl, 4-vinyl or 2-methyl, 5-vinyl pyridine polymers are suitable. The polymers may be obtained commercially.

The metal is found to be firmly bound to the polymers. The polymer contains at least 0.1% metal, generally from 2 to 20% metal by weight. The invention is applicable to all prior homogenous phase transition metal coordination compound catalysts. The ligand coordination group can be supplied by the metal compound and/or by the polymeric support. Exemplary metal complex catalysts are provided in the following table:

TABLE 1

| | |
|---|---|
| $Rh_4(CO)_{12}$ | $Rh_6(CO)_{16}$ |
| $[RhCl(C_2H_4)_2]_2$ | $[Rh(CO)_2Cl]_2$ |
| $RhCl(PPh_3)_3$ | $RhCl_3$ |
| $RhCl_3$ | $H_2PtCl_6$ |
| $RhCl(PHPh_2)_3$ | $Co(CO)_2(PPh_3)_2$ |
| $K_2PdCl_4$ | $RhH(CO)(PPh_3)_3$ |
| Titanocene | $Ru_3(CO)_{12}$ |
| $RhH(CO)(PPh_3)_3$ | $Ru_3(CO)_{10}(NO)_2$ |
| $Ni(CO)_4$ | $Os_3(CO)_{12}$ |
| $Rh_4(CO)_{10}(PPh_3)_2$ | $Mn_2(CO)_{10}$ |
| $Fe(CO)_3(PPh_3)_2$ | $W(CO)_6$ |
| $Cr(CO)_6$ | $Fe(CO)_4PPh_3$ |
| $FeCO_5$ | $Ru(CO)_3(PPh_3)_2$ |
| $Mo(CO)_5PPh_3$ | $Cr(CO)_5PPh_3$ |

These light-activated, supported catalysts can also be utilized for hydrogenation, hydrosilylation, acetoxylation, polymerization and oligomerization addition reactions as follows:

| Reaction | |
|---|---|
| Hydrogenation | $-CX=CX- + H_2 \rightarrow -CXH-CXH-$ |
| Hydrosilylation | $-CX=CX- + SiH \rightarrow -CX(Si)-CXH-$ |
| Hydroformylation | $-CX=CX- + CO + H_2 \rightarrow$ $-CX(CHO)-CXH-$ or $CX(COH)-CXH-$ |
| Acetoxylation | $-CX=CX- + RCOOH \rightarrow$ $-CX(OCOR)-CXH-$ |
| Polymerization | $n(-CX=OX-) \rightarrow -(CX-CX)_n-$ |

The substrate olefin may be an alkene of the formula, $R_1CH=CH\,R_2$ or an alkyne of the formula $R_1C \equiv CR_2$ where $R_1$ and $R_2$ can be aliphatic, aromatic or may be a hydrocarbon or heterocarbon such as ether, ester, acid or the like or $R^1R^2$ groups may be joined to form a cyclic compound. The substrate olefin may be a short chain compound having less than 20 carbon atoms or may be of polymeric length. Representative olefin substrates are provided in the following table:

TABLE II

| ALKENE | CYCLOALKENE | ARENE |
|---|---|---|
| ethylene | cyclohexane | benzene |
| propylene | $\Delta^2$ cholestene | naphthalene |
| but-1-ene | cyclooctene | styrene |
| hex-1-ene | cyclododecene | anthracene |
| pent-1-ene | cycloocta-1,3-diene | |
| vinyl acetate | | |
| styrene | | ALKYNE |
| isoprene | | acetylene |
| butadiene | | hex-2-yne |
| soybean methyl ester | | phenylacetylene |
| trans-pent-2-ene | | |
| vinyl ethyl ether | | |
| isobutene | | |

The photochemical preparation of the catalyst is illustrated schematically in FIG. 1 as contrasted with the reaction in the homogenous phase in absence of ligand containing polymeric support. As shown in the vertical homogenous phase reaction the dimer 10 under the influence of light separates into fragments 12 which coalesce into the tetramer 14 which is an inactive form for addition reactions such as hydroformylation. However, in the photochemical reaction the dimer 10 in the presence of polymer 16 under the influence of light forms a stable associated catalyst 18 in which the fragments 12 are believed to attach to the ligands 20. The hydroformylation reaction may then be practiced in the light or dark by addition of reactants 22 to form aldehydes and regenerated catalyst 24. The catalyst is readily separated from the reaction media.

The photochemical reaction is preferably conducted in a solvent for the transition metal compound which in the case of $Co_2(CO)_8$ can be a liquid alkane such as hexane. The polymer is suspended in the solvent and the dicobalt octacarbonyl or other transition metal compound is added. The metal compound may be present in excess over the amount that binds to the polymer. The excess compound may be removed from the reaction vessel before the addition reaction or may be allowed to remain to provide thermal addition reaction. A part of the excess will be converted to tetramer under the influence of light. The solvent may also be removed by distillation after the metal-polymer adduct is formed. The metal-polymer adduct is sensitive to moisture and oxygen and therefore, the reaction vessel solution and polymer mixture should be rigorously degassed before the reaction. The metal-polymer reaction may also be conducted in the presence of hydrogen and carbon monoxide added to the vessel in the desired ratio. The frequency of the light is critical to formation of an active ambient catalyst. The frequency must be above 250 nm but below 350 nm.

The addition reaction may be conducted in the presence or absence of light. The yield of addition product increases dramatically when the surface area is increased preferably by depositing the polymer or porous, inert, finely divided substrates such as glass beads having a diameter below 1000 microns, preferably 10 to 150 micron, and pores from 50 to 500 nm, preferably no more than 150 nm. Carbon monoxide in great excess can poison the catalyst. The $H_2/CO$ ratio is preferably at least 1.5/1.

Synthesis of Poly 4-vinyl and 2-vinyl Pyridine 4- and 2-vinyl pyridine were copolymerized with or without various cross-linking agents in the presence of water using 0.8 megarads Co-60$\gamma$ radiation. The polymer was obtained in the form of microspheres whose average diameter depended on the initial concentration of the monomer. It was found that presence of cross-linking agent made the beads smaller and regular in shape and less likely to agglomerate. Agglomeration was also reduced on adding 0.4% polyethylene oxide to the solution before polymerization or by increasing the cobalt gamma irradiation dose.

TABLE III

| Run No. | Conc. of 4VP[a] wt/wt & | Wt by Wt Ratio of BAM[b] to 4VP | Size of Beads[c] |
|---|---|---|---|
| 1 | 0.25 | 1:9 | 500 Å |
| 2 | .5 | 1:1 | 900 Å |
| 3 | .7 | 1:2.33 | 950 Å |
| 4 | .9 | 1:3 | 1300 Å |
| 5 | 1.8 | 1:9 | 1600 Å |
| 6 | 2.7 | 1:9 | 2500 Å |

[a]Vacuum distilled from solid KOH; polymerization carried out in degassed solution.
[b]Bis acrylamide; ethylene dimethacrylate was also used and similar results were obtained.
[c]Obtained by scanning electron microscopy; error ± 50%. Average size obtained by taking the mean of 12-20 particles.

Polymerization of 2-vinyl pyridine produced in general smaller beads more resistant to agglomeration even in the absence of cross-linking agents and polyethylene oxide. These polymers were centrifuged, washed in benzene and then the trapped water was removed by azeotropic distillation using benzene. They were then dried in vacuo for 24 hours, washed again in benzene and dried again for 24 hours to yield a white powder.

2-vinyl pyridine was also polymerized on porous glass beads, obtained from Corning Glass Co. These beads were 20–50$\mu$ in diameter and had pores of diameter 150 nm. The glass beads were stirred in the presence of 2-vinyl pyridine for several hours and then wetted with water before being irradiated by Co-60 $\gamma$ rays. It was found that presence of water was essential for appreciable polymerization to occur via this technique. SEM pictures showed that the glass chips were well covered with polymer and the weight percent of polymer incorporated in the chips was obtained by thermogravimetric analysis. The ratio of weight of incorporated polymer to the weight of chips varied from 1.7:1 to 3.6:1. For successful use as a catalyst support system complete coverage of the glass surface by polymers is desirable, since the glass surface is acidic and is expected to destroy catalytic species in contact with it. These were dried as before.

Commercial poly 4-vinyl pyridine was dissolved in dichloromethane and precipitated in benzene. This precipitation was repeated once, and occasionally twice. The polymer was dried as before.

Microspheres of differing porosity were synthesized by varying the amount of cross-linking agent in a 3% total monomer aqueous system containing 4-vinyl pyridine (4 VP) and bis acrylamide (BAM) and subjected to a 0.6 megarad dose of radiation.

Commercial poly-4 VP was dissolved in dichloromethane and precipitated in benzene twice and dried as described above. The porosity of the microspheres was determined by the BET method and standard duration of size was ± 10%. Results follow:

TABLE IV

| Ex. | Total Monomer [M] | 4VP, Wt. % | Surface Area, $m^2/g$ | Diameter, Å |
|---|---|---|---|---|
| 1 | 3 | 95 | 1 | 2500 |
| 2 | 3 | 85 | 1 | 2500 |
| 3 | 3 | 70 | 1.01 | 2500 |
| 4 | 3 | 60 | 47.0 | 2500 |
| 5 | 3 | 50 | 102.0 | 2500 |
| 6 | Commerical Poly-4VP | | 0.3 | — |

The porosity dramatically increases with increasing amount of cross-linking agent as can be seen in Table IV and water absorption also increases with increasing amount of hydrophilic cross-linking agent as shown in the water absorption isotherms.

Catalysis of Hydroformylation Reaction (1) Two Phase Experiments

These experiments were carried out in quartz tubes containing a 20 ml solution of dicobalt octacarbonyl $Co_2(CO)_8$ in n-hexane, suspended polymer particles, and olefins, typically 0.5 M pentene-1. The tubes were prepared by first rigorously degassing the solution and polymer mixture and then irradiated with light from a medium pressure Hg lamp equipped with an IR filter. The tube was connected to a reservoir containing $H_2$ and CO in varying molar ratios. A sample of the gas mixture was withdrawn before and after the reaction for mass spectroscopic analysis. The products were hexanal-1 and hexanal-2 in the ratio of 1:(2.0–2.1). They were analyzed by gas chromatography and absolute yields were calculated by using an internal standard (n-nonane or n-decane).

Figure 2:
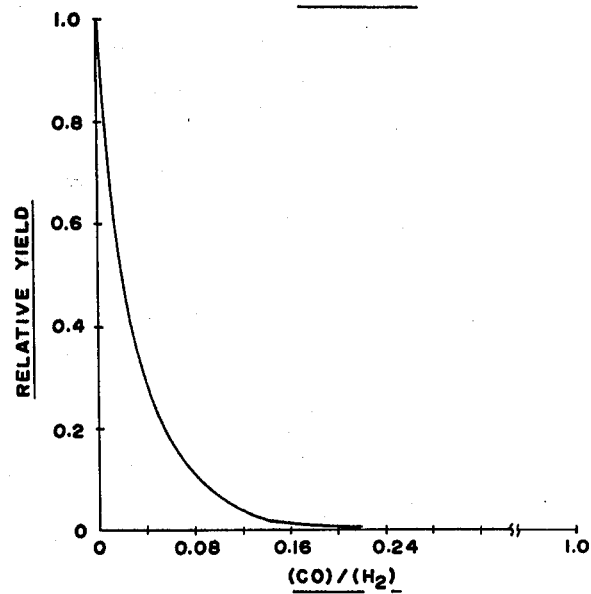
FIG. 2 is a graph of relative yield of aldehyde as ordinate vs $(CO)/(H_2)$ as abscissa in solutions containing phototriggered Co-polymer and free $Co_2(CO)_8$.
Figure 3:
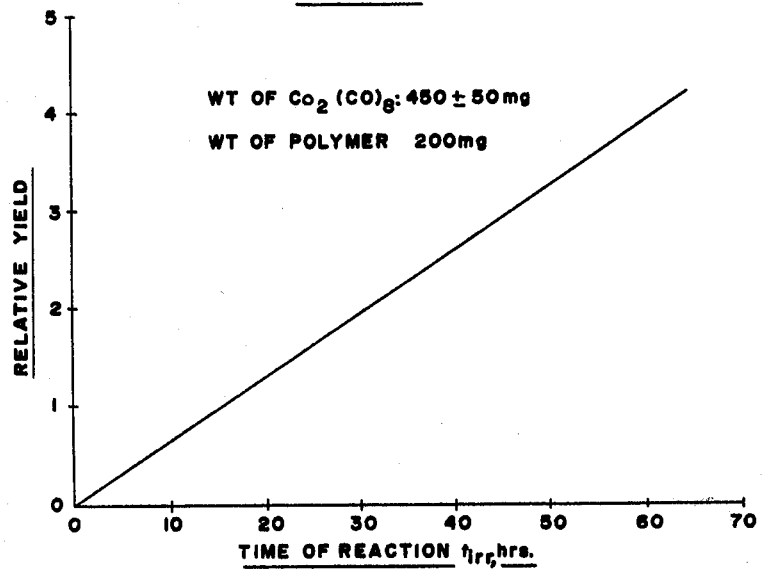
FIG. 3 is a graph of relative yield of aldehyde as ordinate vs. time of reaction as abscissa showing catalyst stability for hydroformylation in hydrogen atmosphere in accordance with the invention.
Figure 4:
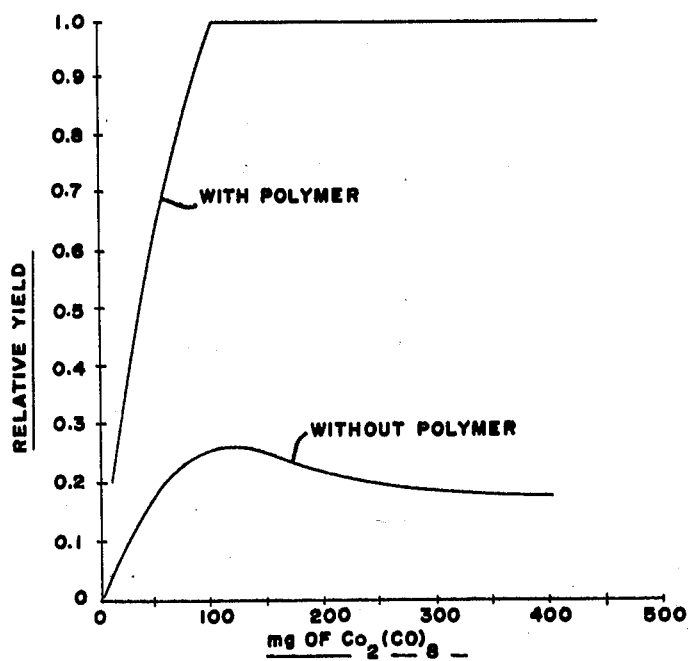
FIG. 4 is a graph of relative yield of aldehyde as ordinate vs. weight of $Co_2(CO)_8$ present as abscissa for hydroformylation in hydrogen atmosphere in the presence or absence of poly-4-VP.
Figure 5:
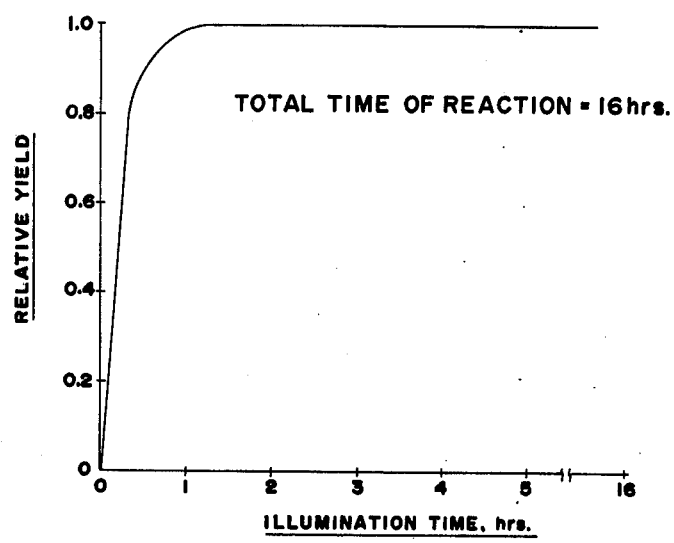
FIG. 5 is a graph of total yield of aldehyde as ordinate vs. initial irradiation period as abscissa.

Yields were studied as a function of $[H_2]/[CO]$ molar ratios (initial). FIG. 2 shows that even relatively small amounts of CO retards the reaction rate significantly. Table V gives the concentrations of reactants and other data on these runs.

tetramer is an inefficient hydroformylation catalyst. For this reason these reactions could be run starting with 100% $H_2$, since the CO needed to form aldehydes would come from decomposition of $Co_2(CO)_8$. Under these conditions yield was measured as a function of time of reaction (FIG. 3), weight of $Co_2(CO)_8$ present (FIG. 4) and irradiation time (FIG. 5).

Once the catalyst is formed the reaction is much less sensitive to CO poisoning, or in other words, presence of CO does not interfere with the action of the polymer bound catalyst, but with its formation. Otherwise, presence of excess of $Co_2(CO)_8$ which leads to increased photoproduction of CO would have inhibited formation of aldehydes. This effect is seen to happen in homogeneous solution phase experiments (in which no polymer was present) run parallel to the two phase experiments, also indicated in FIG. 4. The linearity of the plot in FIG. 3 also supports this conclusion. Experiments were run to demonstrate that the reaction is phototriggered. This was done by varying the period of irradiation followed by a dark reaction period, so that the sum of the total reaction period was constant. Total yield was then plotted (for 16 hours of reaction) vs the initial irradiation period (FIG. 5). The results indicated clearly that the reaction was phototriggered. The uncertainty at the zero time irradiation period probably arises from some dark reaction taking place in the solution phase. Such a dark reaction has been observed in homogeneous phase experiments.

Runs with Isolated Phototriggered Catalyst

In an attempt to isolate the polymer bound catalyst $Co_2(CO)_8$ was removed from the tube after the catalyst was formed. These experiments led to the discovery of the conditions necessary to form the catalyst and also to the fact that the catalytic reaction is phototriggered, i.e. once the catalyst is formed through the reaction of $Co_2(CO)_8$ and the polymer in presence of light, it is an active hydroformylating agent in the dark at room temperature and atmospheric pressure.

At first a solution of $Co_2(CO)_8$ and the polymer was allowed to react in the dark, after which time the excess $Co_2(CO)_8$ was removed by sublimation along with the solvent. Fresh degassed n-hexane was then introduced in the tube along with the olefin. A mixture of $H_2$ and CO in the ratio of 10:1 was fed into the reservoir. No aldehyde formation was observed whether or not the contents of the tube were irradiated. Since it is known that dicobalt octacarbonyl reacts with the polymer in the dark, it seems that the metal-polymer species formed in the dark is not a catalyst. It was expected that this species although not initially a catalyst would be converted to the active species on irradiation. It is possible

TABLE V

| Run No. | $H_2$ Initial Mole % | $H_2$ Final Mole % | CO Initial Mole % | CO Final Mole % | t irr. (hr.) | $Co_2(CO)_8$ mg. |
|---|---|---|---|---|---|---|
| 1 | 89.0 | 83.0 | 7.3 | 12.8 | 15 | 308 |
| 2 | 92.5 | 85.6 | 7.1 | 11.7 | 0 | 300 |
| 3 | 94.1 | 85.1 | 3.67 | 11.9 | 15 | 318 |
| 4 | 100 | 94.4 | 0 | 4.4 | 16 | 430 |
| 5 | 100 | 84 | 0 | 16 | 64 | 536 |

It is obvious that dicobalt octacarbonyl is in large excess since the percent metal attached to polymer is rarely more than 5%. This excess $Co_2(CO)_8$ undergoes photolysis which results in the formation of CO and formation of $Co_4(CO)_{12}$, since homogeneous phase experiments indicate that these are the principal products of photolysis of $Co_2(CO)_8$. They also indicate that the that the cobalt species resting on the surface of the polymer may not receive much light most of which is scattered away.

Reaction of $Co_2(CO)_8$ solutions and polymer in presence of light gave rise to a colored compound which was isolated as before and then tested for catalytic activity in the dark as well as in presence of light. It proved to be an active catalyst under both conditions. This catalyst could also be isolated from two phase experimental runs, by pouring out the solution after a typical 16 hour run, washing the solids left in the tube with n-hexane and introducing fresh solvent olefin mixture. Aldehydes were formed but the yields were poor, indicating that the catlyst which is known to be particularly air sensitive is being partly decomposed during the washing process. A similar air sensitivity of the phosphinated polymer-cobalt catalyst has been observed. Some interesting wavelength effects were observed in this reaction by which the catalyst is formed. These are summarized in Table VI.

TABLE VI

Wavelength Dependence of Catalyst Formation[a]
Light (Wavelength)[b]

| Reaction[c] | Reaction[d] | Yield |
|---|---|---|
| Dark | Dark | No |
| Dark | Light ($\lambda \geq 250$) | No |
| Light ($\lambda \geq 360$)[e] | Dark | No |
| Light ($\lambda \geq 360$) | Light ($\lambda \geq 250$) | No |
| Light ($\lambda \geq 250$) | Dark | Yes |
| Light ($\lambda \geq 250$) | Light ($\lambda \geq 250$) | Yes |

[a] All runs were performed 3 or more times.
[b] Polymers used in these runs were purified commercial poly 4VP, and poly 2-VP on porous glass. Wavelengths given in nanometers.
[c] Initial reaction between $Co_2(CO)_8$ and polymer. Reaction period varied between ½ hour and 1 hours.
[d] Hydroformylation reaction: reactants are olefin, $H_2$ + CO and the polymer bound species. No free $Co_2(CO)_8$ present. Time of reaction = 16 hours.
[e] Light of wavelength $\geq 360$ nm was obtained by using a Uranium glass filler.

ciently under the conditions described above. Acrolein, the sole product, was identified by GC retention times and GC/mass spectroscopy. The conversion of acetylene to acrolein at room temperature and pressure can be utilized in the manufacture of acrylonitrile, since acrolein is readily converted to acrylonitrile through reaction with $NH_3$. Since all raw materials necessary for synthesis of acrylonitrile, e.g. synthesis gas, acetylene and ammonia are available from coal gasification, it is conceivable that this important monomer can be economically manufactured from coal based chemicals.

Spectroscopy of $Co_2(CO)_8$ in solution at room temperature and at low temperature (77° K.) indicate that the 250 nm absorption excites the molecule primarily to the $\sigma^*$ state. Such an excitation leads primarily to photodissociation into a radical pair. In other metal carbonyls, e.g. $Mn_2(CO)_{10}$, the quantum yield of photodissociation increases as the wavelength of excitation approaches the position of the $\sigma^*$ band. Hence it is believed that the photocatalyst is formed by interaction of monomeric cobalt species with the polymer.

Hydroformylation of irradiated hexane solutions containing 1-pentene and $Co_2(CO)_8$ under hydrogen and CO pressures of less than one atmosphere were conducted, the results being shown in the following table. A 1000 W Hg-Xe lamp was used for all these runs. Experiments were run in a quartz tube connected to 500 ml gas reservoir. Yields are not corrected for the thermal formation of aldehydes.

TABLE VII

| Run | $[Co_2(CO)_8]$, M | [1-pentene], M | CO(p,atm) | $H_2$(p,atm) | $t_{irrad}$,[h] | molex hexanal | moles 2-methylpentanal |
|---|---|---|---|---|---|---|---|
| 1 | $1.7 \times 10^{-2}$ | $5 \times 10^{-1}$ | 0 | 0.73 | 24.3 | $2.45 \times 10^{-5}$ | $4.72 \times 10^{-5}$ |
| 2 | $1.5 \times 10^{-2}$ | $8 \times 10^{-1}$ | 0.05 | 0.70 | 15.2 | $1.75 \times 10^{-5}$ | $3.84 \times 10^{-5}$ |
| 3 | $2.4 \times 10^{-2}$ | 1 | 0.12 | 0.63 | 16.9 | $1.06 \times 10^{-5}$ | $2.72 \times 10^{-5}$ |
| 4 | $1.3 \times 10^{-2}$ | $5 \times 10^{-1}$ | 0.23 | 0.50 | 21.8 | $7 \times 10^{-7}$ | $9 \times 10^{-7}$ |

These experiments prove conclusively that the reaction is phototriggered. It is also catalytic, since the amount of metal on the commercial polymer runs were of the order of $1.4 \times 10^{-4}$ moles, whereas yields averaged $2 \times 10^{-3}$ moles using polymer coated glass as support during the time in which the reaction was monitored. The metal carbonyl-polymer species was not losing any significant amount of CO since the moles of aldehyde bound bore an approximate (∼ 10%) correspondence with the amount of CO lost from the reservoir. Yields were measured up to 70% of the initial CO concentration, the reactant present at the smallest concentration.

Effect of Surface Area

The yields of aldehyde rose dramatically (∼ 750%) when the commercial polymer was substituted by polymer on glass chips in the two phase experimental runs. It is believed that this is due to the increase of surface area of the polymer support systems. Increase in surface area of the polymer support could either result in a large amount of cobalt being bound to the polymer or it could stabilize the polymer bonded transition metal species by reducing aggregation caused by chelation of metal sites. Atomic absorption experiments indicate no dramatic increase in cobalt content of the polymer when bound on glass and this indicates that the improved yield may be due to prevention of chelation effects.

Reaction of Acetylene with $H_2$ and CO

In addition to olefins such as pentene-1, hexane-1 and heptene-1, acetylene was found to add $H_2$ and CO effi- Comparison of runs 2 and 4 shows that, as is true in thermal catalytic systems, the reaction is inhibited by carbon monoxide. In fact, the fastest initial rates were observed with no added carbon monoxide (Run 1).

Irradiation of $Co_2(CO)_8$ at 254 nm in hexane solution containing either poly-4- or poly-2-vinyl pyridine yields a brownish-grey powder (Co-PVP). The synthesis of the Co-PVP catalyst is accomplished by about 30 mins of irradiation using a 450 watt medium pressure Hg lamp. Care was taken to remove unattached $Co_2(CO)_8$ from the Co-PVP sample. Attachment of cobalt carbonyl species to polyvinylpyridine can be achieved thermally or by irradiation at longer wavelengths ($\lambda > 350$ nm), but the materials so produced do not catalyze the hydroformylation of olefins at room temperature and atmospheric pressure.

It is assumed that irradiation of $Co_2(CO)_8$ produces CO-deficient species that are trapped by the pyridine residues in the polymer. Gas analysis indicates that the formation of Co-PVP results in the evolution of two molecules of CO from each molecule of $Co_2(CO)_8$ initially present.

Figure 6:
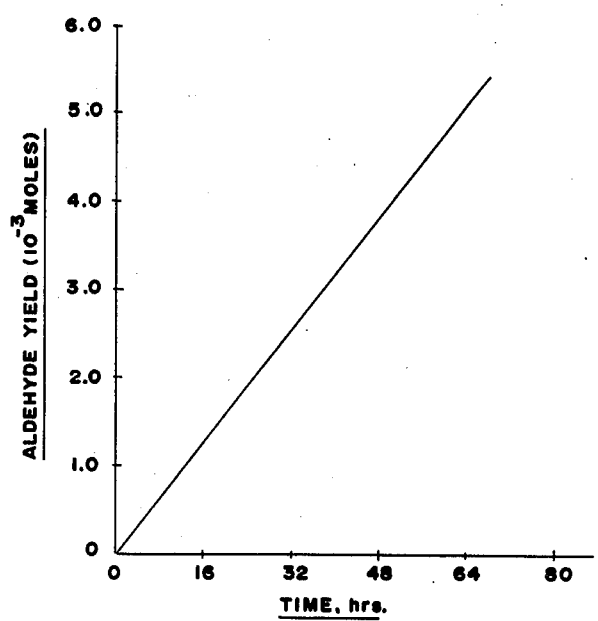
FIG. 6 is a graph of aldehyde yield as ordinate vs. time as abscissa.

A hexane (20 ml) solution of 1-pentene (0.5 ml) and $H_2$/CO (1 atm 0.9/0.1; vol. 106 ml) was hydroformylated in the dark at 25° C. in the presence of Co-PVP (150 mg total/1.2 mg Co) at one atmosphere total pressure. The rate of aldehyde formation is shown in FIG. 6. The phototriggered thermal hydroformylation reaction has been demonstrated to proceed at essentially constant rate for up to 73 hours during which period 3.8

× 10² molecules of aldehyde had been formed per atom of cobalt attached to the polymer. The irradiated Co-PVP was also utilized to form aldehydes from 1-hexene, 2-pentene and to catalyze the conversion of acetylene to acrolein under similar conditions. Ru-PVP and Rh-PVP prepared by ultraviolet irradiation of $Ru_3(CO)_{12}$ and $Rh_3(CO)_{12}$ and poly 4-VP have also been shown to hydroformylate alkenes such as 1-pentene under similar conditions.

The following experimental procedure is employed to synthesize the Rh catalyst for batch reactor runs.

1g of commercial poly-2-vinylpyridine is dissolved in 50 ml benzene and then filtered to remove insoluble impurities. The solution is added dropwise to 250 ml diethyl ether which is vigorously stirred at the same time. The polymer precipitates. It is settled, filtered and then dried. It was redissolved in benzene and re-precipitated in ether. After drying, it is weighed. Yield on purification averages 60-90%. 2.5g of pure polymer is dissolved in benzene (10 ml) and 25.0g of ordinary glass powder or of controlled pore glass (CPG) are added to the solution. The solvent is driven off slowly, with stirring. The material is dried in vacuum at $\sim 50°$ C. and analyzed by TGA.

100 mg of the polymer coated glass is taken in a clean quartz vessel, pumped in the vacuum line at 110° C. for 1 hour and then backfilled with $N_2$. 25 ml of a solution of $Rh_4(CO)_{12}$ in n-hexane (40 mg in 50 ml) is added to the polymer glass composite in the quartz vessel and a reservoir is attached to the vessel. The vessel and the reservoir are then put in the vacuum line and the contents are degassed over 3 cycles. The mixture is then irradiated with light from a Hanovia 450 watt lamp filtered through water for 16 hours with stirring. The mixture is then allowed to settle and the supernatant liquid withdrawn from the vessel under an inert gas. The solids are washed with fresh n-hexane in the vacuum line to remove unreacted $Rh_4(CO)_{12}$. Meanwhile 100 ml of a mixture of n-hexane and 1-pentene (95 to 5 v/v) is degassed in the line. The dark brown Rh-PVP-glass solid (8-10% by weight Rh on PVP) in the quartz vessel is then poured into a stirred Parr pressure reactor whose temperature is maintained at 20° C. The hexane-alkene mixture is added and the reactor is filled with a $H_2/CO$ mixture (80:20 v/v) to 76 psig pressure. The reactor is stirred continuously and samples are withdrawn every two hours. The products are analyzed on a gas chromatograph using a 6 feet × ⅛ inch UCW-98 (5% on chrom W) column. The areas of the peaks are estimated by cutting and weighing. These are compared to calibration peak weights to determine molarity of the products. The concentration is then multiplied by the volume to obtain absolute yields and these are normalized for catalyst weight. The results are shown in the following table:

TABLE VIII

| Run No. | Glass Diameter, Mesh | Glass Pore Size, nm | Activity |
|---|---|---|---|
| 1 | 20-80 | 150 | reasonable |
| 2 | 100-120 | 120-135 | very good 3 times better than 1 |
| 3 | 200 | non-porous | polymer did not attach to substrate |

Figure 7:
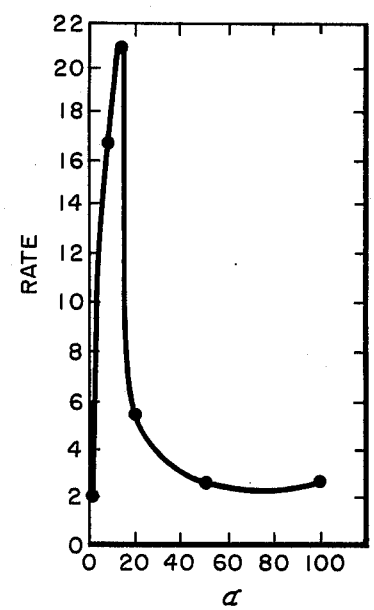
FIG. 7 is a graph illustrating variation of catalytic activity with polymer content of catalyst with Relative Rate ($10^{-5}$ moles of aldehyde per hour per 100mg of catalyst) as ordinate vs. % polymer on chips, $\alpha$ as abscissa.

The above batch runs were repeated varying the ratio $\sigma$, of polymer to glass from 0 to 100%. As shown in FIG. 7 the catalytic activity is strongly dependent on polymer-glass ratio for the photoactivated catalyst. Furthermore, photoradiation is higher when the polymer glass ratio is from 1 to 40% by weight, preferably from 5 to 20% by weight.

Figure 8:
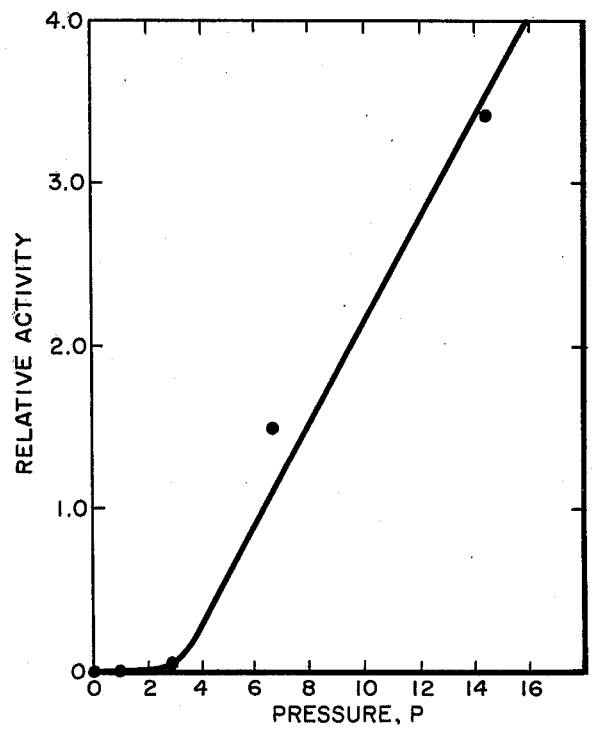
FIG. 8 is a graph illustration variation of catalytic activity with pressure with Relative Activity as ordinate vs. Pressure, P, in atmospheres.

Hydroformylation of a mixture (95:5 v/v) of n-hexane and 1-pentene was carried out in the dark with rhodium-PVP-CPG catalyst (8% Rh-PVP and 10% PVP/CPG) irradiated for 16 hours as described above. The hydroformylations were conducted at 20° C., at $H_2$:CP of 80:20 and at a range of pressures from 1 atm. to 11 atm. Relative activity increased with increasing pressure. It has been observed that lowering the pressure from 90 psi to 20 psi after 24 hours of operation at 90 psi drops the rate but by only 50%. This indicates that the catalyst is formed in situ on reaction between Rh-polymer complex and $H_2/CO+$ olefin under pressure, but once it is formed, pressure requirements are reduced. An extraordinary pressure effect was observed in this reaction as shown in FIG. 8. The rate at 90 psi is about 100-1000 times higher than the rate at 14 psi.

Figure 9:
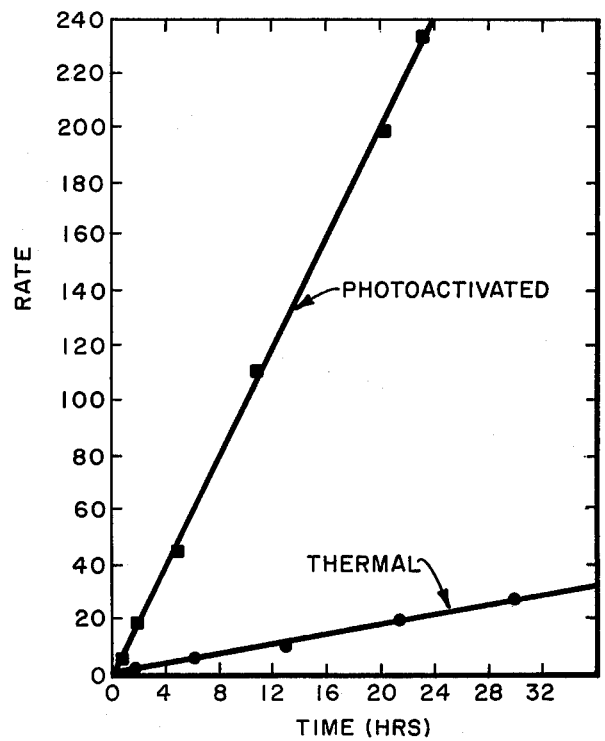
FIG. 9 is a graph of catalyst turnover rate (moles aldehyde formed per hour per mole of rhodium cluster on the polymer) as ordinate vs. time in hours as abscissa for photoactivated and thermally activated $Rh_4(CO)_{12}$—PVP glass supported catalysts.

The rhodium catalysts exhibit significantly higher activity than comparable cobalt catalysts. It has been shown that thermal reaction (at 25° C.) between $Rh_4(CO)_{12}$ solution and the polymer-glass system also produces a catalyst, but the activity of the thermal catalyst is substantially lower than the photochemically synthesized catalyst for certain polymer-glass weight ratios. It has also been shown that while $R_4(CO)_{12}$ is photochemically attached to the polymer, one mole of CO is evolved per mole of $Rh_4(CO)_{12}$ being attached, while no CO is evolved on thermal (dark) attachment. Relative activity is illustrated in FIG. 9. The order of activity being 10 times higher and the evolution of CO from the photochemically prepared catalyst further demonstrates that a different chemical structure is involved in the catalyst of this invention.

Figure 10:
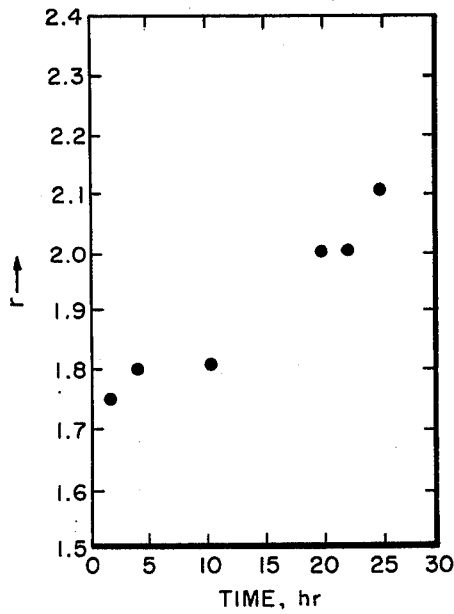
FIG. 10 is a graph illustrating the variation of isomer ratio with time with the ratio, $r$, of linear aldehyde to branched aldehyde as ordinate vs. Time in hours as abscissa.

It has also been observed that the metal carbonyls yield an isomeric mixture of aldehydes which is rich in branched isomer in absence of the polymer. Addition of polymer to these systems produces a 2:1 mixture of linear to branched aldehydes on continuous irradiation, followed by a dark (thermal) reaction which yields almost exclusively the linear aldehyde. The isomer ratio increases in favor of the linear isomer with time. FIG. 10 is a plot of the isomer ratio vs. time. Since the overall yield remains linear, it seems that the sites producing the branched isomer are not decaying, but are undergoing a subtle change in stereochemical environment so that linear isomers are produced.

Hydroformylation experiments with polymer bound ruthenium catalysts were also conducted. Photochemical reaction of triruthenium dodecacarbonyl solutions $[Ru_3(CO)_{12}]$ with polyvinylpyridine and an olefin such as 1-pentene leads to the formation of a yellow powder which can catalyze the hydroformylation reaction. Three types of runs were carried out:

A. $Ru_3(CO)_{12}$ was dissolved in n-hexane (5 mg in 100 ml) and 20 ml of this solution was added to 100 mg of solid polyvinylpyridine in a quartz tube. 1 ml of 1-pentene was added and the mixture was degassed by freeze-pump-thaw (3 cycles). Then a 80:20 mixture of $H_2/CO$ was fed into a reservoir connected to the quartz vessel. The vessel was brought to room temperature and irradiated with ultraviolet ($\geqq 250\lambda$) light while being stirred. The solution was analyzed for aldehydes after 16-24 hours of radiation. Results: Aldehydes were formed in a 2:1 isomer ratio, the linear isomer being the dominant product. Control experiments carried out without radiation produced no yield. Typical yields were of the order of $5 \times 10^{-5}$ moles (total) or a turnover of about 5.

B. $Ru_3(CO)_{12}$ solutions (1 mg in 20 ml n-hexane) were irradiated in the presence of polyvinylpyridine with ultraviolet light for 18 hours in a quartz vessel. The resulting yellow powder was washed and allowed to react with 1-pentene, $H_2$ and CO. There was no aldehyde formation.

C. $Ru_3(CO)_{12}$ solutions (1 mg in 20 ml n-hexane) were irradiated in the presence of polyvinylpyridine and 1-pentene with ultraviolet light in a quartz vessel. After 16 hours of irradiation, the yellow powder was washed and allowed to react with 1-pentene, $H_2$ and CO. Aldehydes were formed in a 2:1 (linear to branched) ratio. Total yields ranged from $1 \times 10^{-3}$ moles to $5 \times 10^{-5}$ moles indicating turnover of 100-5 after 18 hours thermal reaction.

It is to be realized that only preferred embodiments of the invention have been described and that numerous substitutions, modifications and alterations are permissible without departing from the spirit and scope of the invention as defined in the following claims.

What is claimed is:

1. A method of preparing a novel photoactivated catalyst comprising the steps of:
   irradiating a mixture of low valent transition metal coordination compound selected from a carbonyl or phosphine of a metal selected from cobalt, nickel, iron, platinum, rhodium, palladium, manganese, chromium, titanium, tantalum, ruthenium or iridium and a solid polymer polyvinylpyridine support having tertiary amine ligands capable of coordinating with said metal with ultraviolet radiation having a wavelength within the range of 250 to 350 nm; and
   attaching at least 0.1% by weight of said transition metal atoms to said ligands during said irradiation to form a photoactivated catalyst.

2. A method according to claim 1 in which the metal is cobalt, rhodium or ruthenium.

3. A method according to claim 2 in which the metal is rhodium.

4. A method according to claim 3 in which the low valent transition metal compound is $Rh_4(CO)_{12}$.

5. A method according to claim 1 in which from 2 to 20% by weight of metal attaches to the polymer.

6. A method according to claim 1 in which the irradiation step is conducted in the presence of a solvent for the transition metal compound.

7. A method according to claim 6 in which the solvent is a liquid alkane.

8. A method according to claim 6 in which the polymer is insoluble in the solvent.

9. A method according to claim 1 in which the polymer is in the particulate form.

10. A method according to claim 9 in which the polymer is deposited on a high area support.

11. A method according to claim 10 in which the supports are porous glass particles having a diameter below 1000 microns and a pore diameter from 50 to 500 nm.

12. A method according to claim 10 in which the ratio of polymer to support is from 1% to 40% by weight.

13. A catalyst composition produced by the method of claim 1.

14. A composition according to claim 13 in which the polymer is in particulate form.

15. A composition according to claim 14 in which the polymer is deposited on a high area support.

16. A composition according to claim 15 in which the supports are porous glass particles having a diameter below 1000 microns and a pore diameter from 50 nm to 150 nm.

17. A composition according to claim 16 in which the ratio of polymer to support is from 5% to 20% by weight and the ratio of metal catalyst to polymer is from 2% to 20% by weight.

18. A method according to claim 1 in which the mixture is irradiated for at least one-half hour.

19. A catalyst composition according to claim 13 in which the mixture is irradiated for at least one-half hour.

* * * * *